United States Patent [19]

Nudel et al.

[11] 4,446,103
[45] May 1, 1984

[54] METHOD OF DISINFECTING WATER WITH INSOLUBLE DISINFECTANT COMPOSITIONS

[75] Inventors: Ron Nudel, Brooklyn; Gilbert E. Janauer, Binghamton; Eugene E. Schrier, Vestal; Ilona W. Figura, White Plains, all of N.Y.

[73] Assignee: Research Foundation of State University of New York, Albany, N.Y.

[21] Appl. No.: 402,720

[22] Filed: Jul. 28, 1982

Related U.S. Application Data

[62] Division of Ser. No. 117,062, Jan. 31, 1982, Pat. No. 4,349,646.

[51] Int. Cl.³ ............................................. A01N 00/00
[52] U.S. Cl. ........................................ 422/37; 422/28; 525/256; 525/259; 525/333.4; 525/333.6; 525/359.5; 525/359.6
[58] Field of Search ................... 422/28, 37; 525/256, 525/259, 333.4, 333.6, 359.5, 359.6

[56] References Cited

U.S. PATENT DOCUMENTS

| | | | |
|---|---|---|---|
| 2,801,224 | 7/1957 | Green | 525/359.5 |
| 2,828,270 | 3/1958 | Murata | 525/359.5 |
| 3,166,471 | 1/1965 | Gump et al. | 167/33 |
| 3,479,406 | 11/1969 | Wakeman | 210/755 |
| 3,729,457 | 4/1973 | Davankov et al. | 525/359.6 |
| 3,910,862 | 10/1975 | Barabas et al. | 525/359.6 |
| 3,948,853 | 4/1976 | Horning et al. | 210/755 |
| 4,139,459 | 2/1979 | Costin | 525/359.4 |

*Primary Examiner*—Joseph L. Schofer
*Assistant Examiner*—Bernard Lipman
*Attorney, Agent, or Firm*—Omri M. Behr

[57] ABSTRACT

There is provided a water insoluble disinfectant composition comprising a tertiary amine quaternized with a water insoluble carrier to provide a quaternary ammonium salt. In the preferred modification of the invention, the carrier is a resin, most suitably a crosslinked polystyrene or crosslinked methacrylate resin. The compositions of the present invention are formed by creating an amine reactive labile active center on the carrier and reacting said activated carrier with the amine of choice to form a quaternary ammonium salt. Ammonium salts having at least one alkyl moiety of $C_{10}$ to $C_{16}$ carbon atoms and at least one aryl moiety have been found particularly effective.

9 Claims, 2 Drawing Figures

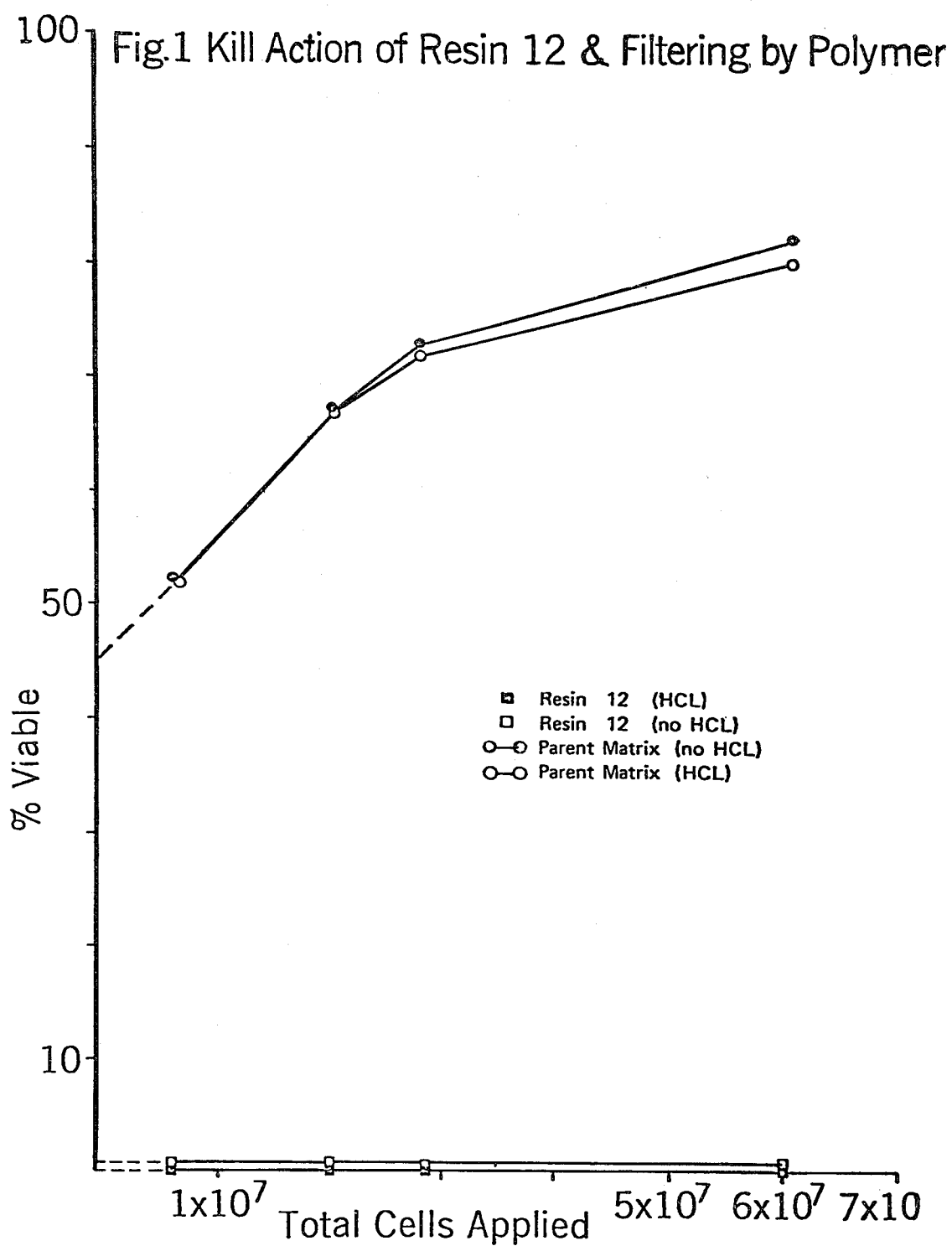

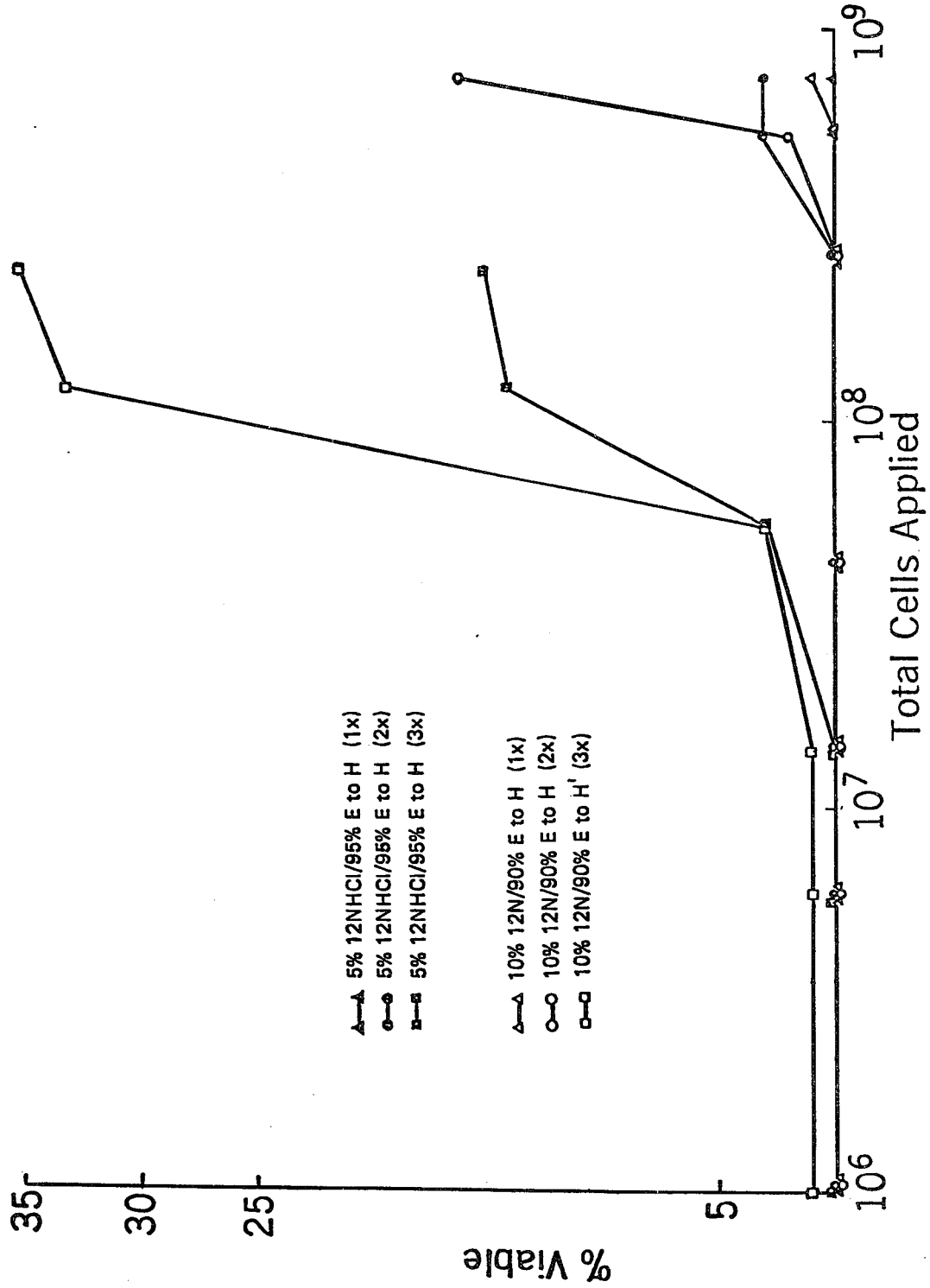

METHOD OF DISINFECTING WATER WITH INSOLUBLE DISINFECTANT COMPOSITIONS

This invention was made with Government support under NSF-SOS Project 240-547A (June 1977) awarded by National Science Foundation. The Government has certain rights in this invention.

This application is a division of application Ser. No. 117,062, filed 1/31/82, U.S. Pat. No. 4,349,646.

BACKGROUND OF THE INVENTION

Heretofore chlorination has been designated as the most reliable water disinfection method and is liable to remain so for the foreseeable future. Nevertheless, in view of the presence of organic compounds in many water sources, chlorination presents the danger of the formation of toxic or carcinogenic substances. Work has, therefore, been directed to seeking alternative modes of drinking water disinfection. A general alternate approach involves strong modes of oxidation for example the use of ozone or the use of ultraviolet radiation. Another oxidizing approach involves the use of the oxidizing power of polyhalide species absorbed on strong base ion exchange resins. These polyhalide counterions release free halogens or hypohalous acids which destroy harmful organisms. Unfortunately, the most effective of these polyhalide species contain iodine, e.g. in the form of the triiodide ion, which is undesirable with respect to dietary intake for certain groups of the population.

A different class of comounds namely the soluble quaternary ammonium salts colloquially known as Quats have been suggested for emergency disinfection of drinking water supplies and, because of their low toxicity for mammals, have been utilized as sanitizers in commercial applications. Because of some inappropriate application of Quats, despite their apparent combination of effectiveness and harmlessness they have fallen into disrepute among medical practitioners, and are now not utilized for the emergency disinfection of drinking water supplies.

It has been postulated that if the soluble Quats could be insolubilized in a procedure which involved stable chemical bonding to an insoluble carrier while retaining their disinfectant qualities a desirable product might be obtained.

SUMMARY OF THE INVENTION

The present invention comprises the provision of stable, water insoluble quaternary ammonium salts. For the sake of convenience these compositions will be discussed with respect to the amine portion and the carrier portion used in the formation of these compositions. As will be seen in the discussion of the preferred embodiments, however, chemically speaking an interchangeability of groups in fact exists. The novel compositions of the present invention are produced by activating a carrier, for example polymeric resin, to provide a labile center thereon which will react with a tertiary or bistertiary amine to provide a stable, water insoluble, quaternary ammonium salt. The anion of said salt may be the anion of any physiologically acceptable acid. Such a designation is one of desirability rather than criticality since the "anion leakage" of these compounds is minimal.

The compositions of the present invention have the following general structure:

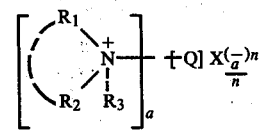

$R_1$ and $R_2$ are alkyl, alkenyl or cycloalkyl or, taken with the nitrogen to which they are attached are a heterocycle. $R_3$ where present is alkyl, alkaryl, aralkyl or aryl, Q is the carrier moiety bonded to the ammonium nitrogen, a is an integer corresponding to the number of ammonium moieties per carrier moiety, x is the counterion of any physiologically acceptable acid having valence n, wherein n is an integer. Any one of $R_1$ $R_2$ or $R_3$ may itself represent a quaternary ammonium moiety of the substructure.

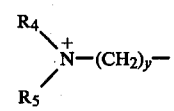

wherein $R_4$ and $R_5$ may have any of the values of $R_1$, $R_2$ or $R_3$ and y is an integer of 1-20.

It will be understood by those skilled in the art that where $R_1$ and $R_2$ form a fully unsaturated heterocycle with the nitrogen to which they are attached, $R_3$ cannot be present.

The modification of this invention where the carrier was a halomethylated polystyrene (crosslinking not shown) may be shown as

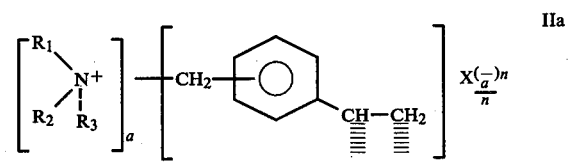

wherein a and n are as above and n is an integer.

Where the initial amine is a bistertiary amine the corresponding modification may be shown as

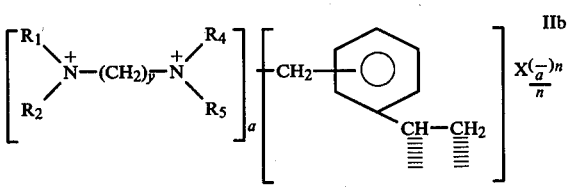

Similarly where the carrier was a halomethylated methylmethacrylate (crosslinking not shown) a modification of the invention may be shown as

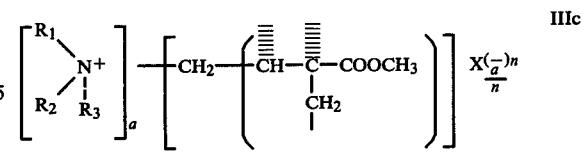

DESCRIPTION OF THE PREFERRED EMBODIMENTS

The compositions of the present invention are prepared by activating a carrier to provide a labile center reactive with the tertiary amine of choice. In view of their physical characteristics their ready commercial availability and comparatively low cost as well as their potential, under certain circumstances, to be regenerated, polymer resins form a useful class of carrier although the invention should not be considered as limited thereto.

The majority of polymeric resins have a polystyrene backbone. A further readily available although minor category of polymeric resin has a methyacrylate backbone. The resins may be prepared in microporous or macroporous structural form.

The most readily available polystyrene resins are crosslinked with certain crosslinking agents among which the most common is divinylbenzene (DVB), although again the invention is not considered to be limited to the use of particular crosslinking agent.

The skeletal matrix of the resin, suitably of the DVB crosslinked polystyrene resin is then activated to provide a labile center which will react with the tertiary amine. An inexpensive and readily available labile group is the chloromethyl group. Chloromethylating agents and the mode of reacting them with a polymeric skeletal matrix are well known in the art. Indeed, chloromethylated DVB crosslinked polystyrene resin is commercially available.

The chloro moiety of the chloromethyl group will provide the counterion of the quaternary ammonium salt ultimately produced. Thus, if it is desired to utilize a counterion other than chloride, it can be introduced later by simple and conventional ion exchange procedures. From the point of view of safety, the anion of any pharmaceutically acceptable acid may be utilized as the counterion. While, from the point of view of safety any pharmaceutically acceptable anion may be employed, for example hydrochloric, hydrobromic hydriodic, sulphuric, phosphoric, nitric, acetic, propionic, lauric, benzoic, salicyclic, cinamic, lactic, maloic, fumaric, pyruvic, glutamic, oxalic, methane sulphonic, benzene sulphonic, glucose-1-phosphoric, or the like, from the point of view of effectiveness halide, suitably chloride, bromide and iodide have been found to be totally effective in the tests for effectiveness which have been carried out are especially preferred.

The amine reagent utilized is a tertiary amine or a bistertiary aminoalkane having the general structure

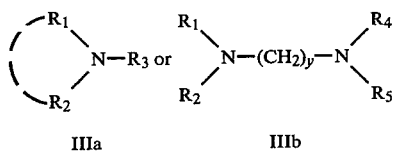

$$\begin{array}{cc} R_1 \diagdown & R_1 \diagdown \diagup R_4 \\ N-R_3 \text{ or } & N-(CH_2)_y-N \\ R_2 \diagup & R_2 \diagup \diagdown R_5 \\ \text{IIIa} & \text{IIIb} \end{array}$$

$R_1$ and $R_2$ may be the same or different and may be alkyl, alkenyl or cycloalkyl, suitably straight or branch chain lower alkyl of one to eight carbon atoms suitably methyl, ethyl, propyl, isopropyl, butyl, n-butyl, isobutyl, pentyl, oxalyl or the like, straight or branch chain lower alkenyl of two to six carbon atoms such as ethenyl, propenyl, isopropenyl, butenyl, isobutenyl, tert-butenyl, pentenyl, hexenyl and the like or cycloalkyl of three to six carbon such as cyclopropyl, cyclobutyl, cyclopentyl or cyclohexyl. Also included are the corresponding cycloalkenyl moieties of four to six carbon atoms, either $R_1$ or $R_2$ may have the values of $R_3$ below.

$R_1$ and $R_2$ may also be joined together to yield in conjunction with the nitrogen atom to which they are attached a heterocyclic moiety of five to seven atoms in the ring. This heterocyclic moiety may be saturated, partially unsaturated, or fully unsaturated that is to say aromatic. Included in this category would be aziridyl, pyrrolidyl, pyrrolyl, pyridyl, piperidyl, azepinyl, perhydroazoinyl and the like.

Of the foregoing, the pyridyl moiety is particularly preferred. The foregoing heterocyclics may, if desired, be substituted by alkyl moieties appropriate to the $R_1$ and $R_2$ groups constituting the carbon portion of the heterocyclic ring.

$R_3$ may be alkyl, suitably midalkyl of ten to sixteen carbon atoms which may be straight or branch chain, the former being preferred. $R_3$ may also be aryl, alkaryl, or aralkyl. The aryl moieties may be carbocyclic or heterocyclic, suitable carbocyclic, such as phenyl or naphthyl, similarly the alkaryl moieties may be carbocyclic or heterocyclic and are suitably substituted by lower alkyl substituents containing 1-5 carbon atoms. These substituents may number from one to the maximum available number of positions on the ring. Thus, where the aryl moiety is phenyl, there may be from 1-5 substituents and where the aryl moiety is naphthyl there may be from 1-7 substituents; with respect to the aralkyl moieties, the aryl portion may be carbocyclic or heterocyclic, suitably carbocyclic, and may be substituted or unsubstituted phenyl or naphthyl. The substitution is, suitably, by halogen or lower moieties of 1-6 carbon atoms located at from one to the maximum number of available positions on the ring. Similarly, the alkyl segment of the aralkyl moiety is suitably lower alkyl of 1-6 carbon atoms.

The disinfectant compositions of the present invention in the form of quaternary ammonium salts are prepared by reacting the amine of general formula (IIIa) or (IIIb) above with the activated carrier, suitably the activated crosslinked polymeric resin where the resin is a crosslinked polystyrene or crosslinked polymethylmethacrylate. Most suitably the reaction is carried out with commercially available chloromethylated divinylbenzene crosslinked polystyrene.

In this procedure the activated polymeric resin is swelled prior to amination suitably by immersion in an excess of water miscible reaction inert organic solvent, suitably an alkanol, a ketone or a water miscible ether preferably a cyclic ether such as dioxane. The resin is immersed, suitably at ambient temperature, for from about 24 to about 60 hours. The mixture in the solvent is cooled to under about 5° C. suitably to between −10° C. to about +5° C. and an excess (based on active centers on the resin) of the amine of choice is added.

The amine is, suitably, pre-cooled to the temperature of the resin/solvent mixture. Where the amine does not dissolve readily in the swelling solvent upon agitation, the entire mixture is warmed just enough to permit solution of the amine, re-cooled to the aforementioned range, and retained at that temperature for about 24 to about 60 hours suitably for about 48 hours.

The aminated resin is then separated, suitably by filtration. It is held in dilute acid suitably dilute mineral acid such as aqueous hydrochloric acid at ambient temperatures, suitably for from about 24 to about 60 hours, and then washed alternately with aqueous acid and aqueous base suitably dilute hydrochloric acid and dilute sodium hydroxide followed by aqueous saline and finally deionized distilled water in which it is stored.

The resulting material is then cycled in acid and base, suitably in dilute aqueous hydrochloric acid and dilute aqueous sodium hydroxide, and then washed, first with several portions of dilute aqueous sodium chloride and finally with deionized, distilled water until the effluent is free of chloride ion.

The quaternary ammonium salts in resin form prepared in accordance with the foregoing procedures may be utilized to disinfect drinking water by any contact method known to the water purification art. The preferred mode, however, is to prepare a bed of the composition, suitably in column form, but not being restricted thereto, and causing the water which is to be disinfected to pass through the column.

In accordance with accepted water purification techniques, it is desirable to remove as much solid or colloidal material as possible prior to contact with the resin. This may be done by any prefiltration method known to the water purification art among which may be included filtration through sand, charcoal (in activated or other form), sintered glass, glass fiber beds, or any other suitable and available pre-filtration medium. The material of the present invention is effective not only against bacteria and viruses, but also against fungi, algae and protozoa.

Observations indicate that when a carrier bed loses its effectiveness as a disinfectant medium that loss is not due to chemical reactions or loss of reactive groups on the bed but rather to the blocking of the active sites by the debris of the biological material. The bed can therefore be regenerated by removing this absorbed microscopic debris from the surface and interstices of the disinfectant composition.

It has been found that the resin may be regenerated by treatment with aqueous alkanolic acid, suitably with mixtures of ethanolic aqueous hydrochloric acid, suitably by utilizing between 6 and 12 N aqueous hydrochloric acid in an HCl:EtOH ratio of between 1:19 to 3:17. The mode of regeneration of the resin should not be considered to be limited to this method.

The results of bactericidal tests carried out on a disinfectant composition within the scope of the present invention N,N-dimethyldodecyl ammonium/(methylated/DVB crosslinked polystyrene) chloride are illustrated in FIG. 1. This test indicates that utilizing a 1 ml bed of 0.8 cm$^2$ cross-section a total kill was noted up to an applied level of $5.8 \times 10^7$ microorganisms (viz: *B. subtilis*). In another experiment no viable cells emerged from the bed until $8.2 \times 10^8$ cells of a total of $9.4 \times 10^8$ cells had contacted the resin bed and thereafter less than 1% of the additionally applied bacteria emerged in viable form. In contrast, where the parent polymer resin itself is utilized without quaternizing with the amine moiety, the percentage viability for between $10^7$ and $6 \times 10^7$ applied cells ranges from approximately 50% to approximately 80%, indicating that some absorption but no real disinfection occurs.

EXPERIMENTAL

Preparation of Resin Material

Chloromethylated crosslinked polystyrene (5 g, 200–400 mesh, 2% divinyl benzene) is immersed in dioxane (250 ml) for 48 hours at ambient temperature (ca. 20° C.). The mixture is cooled to 0° C. and N,N-dimethyl dodecyl amine (75 ml), precooled to 0° C. added. The mixture is warmed slightly to dissolve the amine and is then cooled again and held at 0° C. for 48 hours with intermittent stirring. The mixture is filtered, the filtrate discarded and the residual resin suspended in dilute aqueous hydrochloric acid (75 ml, 2M) for 48 hours at ambient temperatures. The resulting suspension is again filtered and the resin washed with three cycles of aqueous hydrochloric acid (2M, 50 ml × 3) and aqueous sodium hydroxide (0.1M, 50 ml × 3), thereafter with dilute saline (2M, 25 ml × 5) and with deionized, distilled water until the effluent is free of chloride. The resultant quaternary ammonium salt in resin form is stored in deionized distilled water.

In accordance with the above procedure, but where in place of N,N-dimethyldodecyl amine there is utilized N,N-dimethyldecyl amine, N,N-dimethylmyristyl amine, N,N-dimethylbenzylamine, N-dodecyl-N-methyl-3,4-dichlorobenzylamine, quinoline, isoquinoline, pyridine N-N-didecylmethylamine, N-octyl-N-decylmethlamine, N-cetyl-N-dimethylnaphthylamine, a similar composition is obtained.

In accordance with the above procedure, but where in place of the tertiary amines set forth above there is utilized 1, 10-bis(N,N-dimethylamino)decane or 1,2-bis(N,N-didodecylamino)ethane, there is obtained a similar product.

In accordance with the above procedure and using any of the aforementioned amines but utilizing the resins in macroporous form, a similar product is obtained. Further, in accordance with the above procedure but utilizing in place of a polystyrene resin a methylated crosslinked polymethylmethacrylate resin in macro porous or micro porous form there is obtained the corresponding product.

TEST PROCEDURES

Preparation of Test Solutions

*Bacillus subtilis* (NP-40) was grown at 40° C. for 14–16 hrs in Buffered Glucose Broth. The cells were centrifuged at 24° C. (5000 rpm/7 min) in a Sorval Superspeed RC-2 Automatic Refrigerated Centrifuge. The pellet was suspended in sterile Tris buffer (pH 7.6, 250 ml, 0.01 M). Samples of this suspension (10 ml) were diluted with more buffer up to total volumes of 2000 ml. Prior to each experiment a control solution was maintained under identical conditions to the test solutions.

Preparation of Resin Bed

Resin prepared in accordance with Example 1 as well as control materials i.e. (Dowex 1X2 and the parent chloromethylated divinylbenzene crosslinked polystyrene) were slurried in deionized distilled water. 1 ml of deionized distilled water was added to a 6 cm. × 0.8 cm$^2$ fritted glass column and the meniscus marked on the column. The slurried resin was added so as to settle into a bed to the height of the mark. The resin of Example 1 was utilized in chloride form except where indicated to the contrary.

Test Method

The test solutions were run through the column at flow rates of between 10 and 12 ml/min. Effluents were collected in 100 ml fractions at pre-designated intervals in 100 ml fractions (monitored at 200, 400, 800, 1200, 1500, 1800, 1900, 2100 and 2300 ml points). Collection was in sterile enclosed beakers. Portions of diluted and undiluted effluent were plated out on Nutrient Agar and incubated overnight at 40° C. Thereafter the plates were examined for viable cells. The test results of various batches of the N,N-dimethyldodecyl ammonium/-(methylated/DVB crosslinked polystyrene) chloride of Example 1 are summarized in Table I below.

Comparative tests with the chloromethylated divinylbenzenepolystyrene resin itself (i.e. without quaternization) or with the chloride form of a polystyrene benzyltrimethyl ammonium ion exchange resin (Dowex 1 type) show no anti microbial activity although in preliminary experiments a slight reduction in the number of viable cells is noted due to a "filtration" effect.

Effect of Other Counterions

The chloride counterion of the principle composition of Example 1 was displaced with the following ions: bromide, iodide, thiocyanate, ethanesulfonate, n-pentane sulfonate by passing an aqueous solution of the corresponding sodium salt through the column.

Test experiments in accordance with the foregoing procedures but utilizing an application of 1600 ml of test solution containing $2.4 \times 10^9$ cells of *B. subtilis* per charge yielded the following proportion of viable cells in the last 100 ml fraction.

Bromide: 0
Iodide: 0
Thiocyanate: 33%
Ethanesulfonate: 10%
N-pentane sulfonate: 1%

The resin, after exhaustion (arbitrarily defines as 50% viable of *B. subtilis* organisms to pass therethrough) was regenerated by passing through the column a mixture of aqueous hydrochloric acid (12N) and ethanol in a ratio of both 1:19 and 2:9 followed by sterile Tris hydrochloride buffer (pH 7.6, 250 ml, 0.01 M). The regenerated columns were then resubjected to passage of *B. subtilis* suspension as set forth above.

The results are summarized in FIG. 2.

TABLE I

Kill Capacity of Resin 12

| Temperature | Resin Batch | Amount Cells Applied | Kill Capacity* | % Viable of Total |
|---|---|---|---|---|
| 24° C. | 1 a | $9.4 \times 10^8$/2300 ml | $8.2 \times 10^8$ | <1 |
|  | b | same | same | same |
| 35° C. | 1 a | $9.6 \times 10^8$/1800 ml | ≧total | 0 |
|  | b | same | same | same |
| 24° C. | 2 a | $9.4 \times 10^8$/2300 ml | ≧total | <1 |
|  | b | same | same | same |
| 24° C. | 3 a | $2.4 \times 10^9$/1600 ml | ≧total | 0 |
|  | b | same | same | same |

*Operationally defined as the total number of cells applied to first appearance of viable cells in column effluent.

We claim:

1. A method of disinfecting water which comprises contacting the water to be disinfected with a water insoluble disinfectant composition comprising a quaternary ammonium salt of the formula:

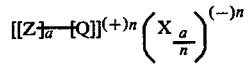

wherein
a is a positive integer,
n is an integer of 1–6,
Q is a water insoluble crosslinked resin of microporous or macroporous structure selected from the group consisting of polystyrene resins having methylene moieties attached to the backbone thereof, and methylated poly methyl acrylate resins,
X is the anion of any physiologically acceptable salts, and
Z is

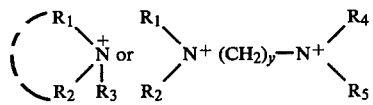

wherein:
$R_1$ and $R_2$ are selected from the group consisting of straight or branch chain lower alkyl of one to eight carbon atoms, straight or branch chain lower alkenyl of two to eight carbon atoms, lower cycloalkyl of three to six carbon atoms and $R_3$, and $R_1$ and $R_2$ when taken together with the nitrogen to which they are attached, form a saturated or unsaturated heterocycle having five to seven carbon atoms in the ring,
$R_3$ is straight or branch chain midalkyl of ten to sixteen carbon atoms, phenyl, halo or lower alkyl substituted phenyl naphthyl lower alkyl and halo or lower alkyl substituted naphthyl lower alkyl wherein said lower alkyl moieties are of one to five carbon atoms and are substituted on from one to five positions on the phenyl nucleus and from one to seven positions on the naphthyl nucleus,
$R_4$ and $R_5$ are selected from the same group of values as $R_1$-$R_3$,
y is a positive integer of 1–20, provided that where $R_1$, N, and $R_2$ are joined to form a saturated or a unsaturated heterocycle, $R_3$ is absent, and
Z is bonded to the methylene moieties.

2. A method according to claim 1 wherein the resin is a divinylbenzene crosslinked polystyrene resin.

3. A method according to claim 1 having methylene moieties attached to the resin backbone said methylene moieties being bonded to the ammonium nitrogen.

4. A method according to claim 1 wherein $R_1$ and $R_2$ are each methyl and $R_3$ is a midalkyl of ten to sixteen carbon atoms and X is halide.

5. A method according to claim 1 wherein Z is pyridinium, quinolinium or isoquinolinium.

6. A method according to claim 2 wherein the moieties are attached to the resin backbone, Z is N,N-dimethyldodecyl ammonium, and said methylene moieties are bonded to said ammonium nitrogen.

7. A method of claim 1 wherein Z is an alpha, omega-ditertiary ammonium alkane.

8. A method of claim 7 wherein Z is 1,2-bis(didocedyl ammonium) ethane.

9. A method of claim 1 wherein Z is N-cetyl-N-dimethylnaphthyl ammonium.

* * * * *